United States Patent [19]

Tanaka et al.

[11] Patent Number: 5,112,750
[45] Date of Patent: May 12, 1992

[54] IMMOBILIZED CELLS AND CULTURE METHOD UTILIZING THE SAME

[75] Inventors: Hideo Tanaka, Niiharigun; Masatoshi Matsumura, Tsukubagun; Satoru Harada, Tsukubagun; Mizuo Yajima, Tokyo, all of Japan

[73] Assignee: Asama Chemical Co., Ltd., Tokyo, Japan

[21] Appl. No.: 748,473

[22] Filed: Jun. 25, 1985

[51] Int. Cl.$^5$ .............. C12N 11/02; C12N 11/10; C12N 11/14; C12N 11/08
[52] U.S. Cl. .................. 435/177; 435/178; 435/176; 435/180; 435/182; 435/161
[58] Field of Search ............. 435/161, 162, 176, 177, 435/178, 182, 180

[56] References Cited

FOREIGN PATENT DOCUMENTS

| 2912827 | 10/1980 | Fed. Rep. of Germany | 435/182 |
| 2055121 | 2/1981 | United Kingdom . | |
| 2113248 | 8/1983 | United Kingdom | 435/161 |

Primary Examiner—Douglas W. Robinson
Assistant Examiner—Irene Marx
Attorney, Agent, or Firm—Birch, Stewart, Kolasch & Birch

[57] ABSTRACT

Novel immobilized cells are prepared by immobilizing microbial cells in a gel carrier wherein an absorbent for organic solvents harmful to the cells is dispersed. A method for normally culturing these immobilized cells is utilized in a medium that contains the organic solvents or to which organic solvents are added without any previous sterilization. The present invention makes it possible to realize an ideal fermentation process without requiring a sterilizing process.

21 Claims, No Drawings

IMMOBILIZED CELLS AND CULTURE METHOD UTILIZING THE SAME

BACKGROUND OF THE INVENTION

This invention relates to novel immobilized cells and a culture method utilizing them. More particularly, it relates to immobilized cells prepared by immobilizing microbial cells in a gel carrier and dispersing an absorbent for organic solvents harmful to the cells therein as well as to a method of normally culturing the cells in a medium which already contains harmful organic solvents or to which said solvents are added.

In fermentation industry, the expense of materials to be fermented accounts for a significant part of the total cost so that the more inexpensive materials are the more preferable. However such materials are frequently contaminated with anti-microbial substances harmful to microbial cells. In the case of mass culture in a large tank with the a large amount of water, it is preferable from an economical viewpoint to reuse the post-fermentation culture liquor since a large amount of waste liquor should be treated and a significant part of the constituents of the medium remain therein. However the culture liquor is unavoidably contaminated with various antimicrobial substances including organic solvents used in the process for extracting the culture product from the medium and in crystallizing the same. In addition, it is frequently impossible to treat waste water caused by not only fermentation methods but also various chemical industrial processes, such as activated sludge methods, since the waste water is contaminated with various substances which are harmful to constituent cells contained in the activated sludge.

In the above-mentioned cases, it is necessary to remove these antimicrobial substances to normally culture the cells. Thus we have directed our attention to organic solvents among these antimicrobial substances and have tried to establish a culture method whereby cells can maintain normal vital activity even in the presence of these solvents.

On the other hand, one distinction between the fermentation and other chemical industries is that in the former attention should be paid to the prevention of contamination with infectious microbes when creating pure cultures of a single, microorganism. That is, it is necessary to previously sterilize the medium and apparatus to be employed by, e.g. heating to 120° C. at 1 atm for 10 to 30 min. It is further necessary to give much attention to the prevention of contamination by infectous microbes throughout the culture, which results in additional cost. Furthermore the apparatus itself should stand elevated pressure and temperature levels, and be equipped with a condenser, which brings about enormous expenses in construction and maintenance. Under these circumstances, fermentation without any sterilizing process has been a long-cherished dream of the fermentation industry and considered an "ideal fermentation" method for a long time. In order to realize the ideal fermentation method, we have tried to develop a method for normally culturing particular cells while preventing the growth of infectious cells with substances harmful only to the latter cells.

SUMMARY OF THE INVENTION

As a result we have found that immobilized cells can maintain normal vital activity for a long time even in the presence of harmful organic solvents by cultureing these immobilized cells in a gel carrier wherein the cells and an absorbent for the organic solvents are dispersed at the same time. We have further found that the immobilized cells can maintain normal vital activity for a long time without being contaminated with any infectious microbes in a medium to which organic solvents harmful to the cells are added without sterilization of the medium and apparatus. Based on the above findings, we have further carried out detailed studies and established novel immobilized cells having preventive functions against harmful organic solvents, i.e. antimicrobial substances, as well as a culture method utilizing the same, thus completing the present invention.

It is an object of the present invention to prepare immobilized cells which have protective functions against organic solvents harmful to microbial cells and which can maintain normal vital activity even in the presence of these solvents.

It is another object of the present invention to establish a convenient and economical method for normally culturing cells wherein the immobilized cells of the present invention are utilized in a medium that contains harmful organic solvents without previously removing these solvents or to which harmful organic solvents are added in order to thereby prevent the growth of infectious microbes without previously having to sterilize the medium or apparatus to be used.

DETAILED DESCRIPTION OF THE INVENTION

Any microbial cells such as bacteria, yeasts or fungi may be employed in the present invention.

Absorbents of organic solvents that are harmful to the cells may be either liquid or solid. Examples of these absorbents are chemicals harmless to the cells, such as lipids, e.g. long-chain hydrocarbons, fatty acids, glycerides and derivatives thereof, wax esters, phospholipids, and glycolipids and organic solvent absorptive carriers such as active carbon, acid clay, alumina, silica gel or synthetic exchange resins. Examples of the glycerides are castor oil, soybean oil, olive oil, tung oil, linseed oil, sesame oil, peanut oil and rape seed oil. Examples of the fatty acids are constitutive unsaturated fatty acids of vegetable oils as noted above, such as oleic acid, erucic acid, linolic acid, linolenic acid and ricinoleic acid. Examples of organic solvent absorptive carriers include Porapak Q (mfd. by Water Associates Inc.), which is a packing for gas chromatography, and silica gel.

These absorbents for organic solvents may be used in an amount of 0.1 to 15% based on the gel carrier. The amount thereof strictly depends on the absorbent, cells and immobilizing material. In order to carry out the method more effectively, it is preferable to ground a solid absorbent as finely as possible.

Any conventional materials capable of forming a gel may be used in immobilizing the cells and the absorbent for organic solvents. For example, natural materials such as alginates, κ-carrageenan, agar, collagen and gelatin and synthetic materials such as polyacrylamide, photocrosslinked resins, prepolymers and urethane polymers may be employed.

Immobilization may be performed in a conventional manner. For example, an aqueous solution containing an alginate is thoroughly mixed with cells and an absorbent for organic solvents and subsequently the alginate is converted into a water-insoluble salt in a conventional manner to thereby immobilize the cells and the absorbent in the same gel carrier. The cells thus immobilized have preventive functions against organic substances harmful thereto and can maintain normal vital activity for a long time. Furthermore, the immobilized cells can be normally cultured for a long time without being contaminated with infectious microbes in a medium to which organic solvents harmful to the cells are added without previously sterilizing the medium and apparatus.

Any organic solvents exerting an antimicrobial effect, such as 2-octanol, toluene or benzene, may be used in the present invention.

To further illustrate the present invention, the following examples are given.

EXAMPLE 1

200 ml portions of a glucose medium comprising 5% of glucose, 0.2% of ammonium sulfate, 0.5% of yeast extract, 0.5% of $KH_2PO_4$ and 0.005% of $MgSO_4 \cdot 7H_2O$ (pH 5.0) were introduced into Erlenmeyer flasks of 500 ml in volume and each inoculated with an yeast strain different from each other. 0.1% of various organic solvents conventionally used in alcoholic extraction were added thereto and each strain was cultured at 100 rpm and 30° C. for 24 hours. The multipliability and glucose consumption of each strain were determined and compared with control data obtained by adding no organic solvent. Table 1 shows the result wherein each value represents a relative % calculated by defining the multipliability or glucose consumption of each strain in the absence of organic solvents as 100%.

TABLE 1

| | Effect of organic solvent on multipliability and glucose consumption of yeasts | | | | | |
|---|---|---|---|---|---|---|
| | Organic solvent | | | | | |
| | 2-octanol | | 3-phenyl-1-propanol | | trinitrobutyl-phosphate | |
| Yeast strain | Multi-pliability | Consumption | Multi-pliability | Consumption | Multi-pliability | Consumption |
| Saccharomyces cerevisiae ATCC 26603 | 2% | 22% | 50% | 100% | 80% | 100% |
| Saccharomyces uvarum ATCC 26602 | 0.5 | 10 | 60 | 100 | 83 | 100 |
| Saccharomyces sake yabe IFO 0309 | 1 | 12 | 58 | 100 | 75 | 110 |
| Zygosaccharomyces pombe IFO 0344 | 2 | 3 | 75 | 100 | 5 | 10 |
| Candida brassica IFO 01664 | 2 | 10 | 55 | 100 | 90 | 100 |

Table 1 indicates that 2-octanol is harmful to all of the yeast strains used. Thus addition of 0.1% of 2-octanol to a medium may be effective in inhibiting multiplication of bacteria to thereby prevent putrefaction caused by infectious microbes.

Subsequently 10 ml portions of a yeast strain (Saccharomyces cerevisiae ATCC 26603) cultured for 16 hours and 6 ml portions of various vegetable oils (i.e. absorbents for 2-octanol) were added to 84 ml portions of a 2% sterilized aqueous solution of sodium alginate and thoroughly admixed therewith. Each mixture was added dropwise through a nozzle to a 100 mM solution of calcium chloride to thereby form spherical immobilized cells (diameter mm). 20 g of the immobilized cells thus prepared and 0.4 g of calcium chloride were added to 200 ml of a glucose medium in an Erlenmeyer flask of 500 ml in volume and cultured therein at 100 rpm and 30° C. for 16 hours. Then the immobilized cells were taken out from the medium and added to 200 ml of a fresh glucose medium in an Erlenmeyer flask of 500 ml in volume. 0.1% of 2-octanol (i.e. a harmful organic solvent) was further added thereto and the cells were cultured under the same condition as described above. Table 2 shows the result wherein each value represents a relative % calculated by defining the glucose consumption or alcoholic fermentability of the strain in the absence of 2-octanol as 100%. Immobilized cells containing no vegetable oil were employed as a control. Figures in parentheses indicate culture periods.

After culturing for six hours, the control immobilized cells to which no 2-octanol was added entirely consumed the glucose, thus completing the alcoholic fermentation.

TABLE 2

| Effect of 2-octanol on glucose consumption and alcoholic fermentability of immobilized cells containing vegetable oil | | |
|---|---|---|
| Vegetable oil | Glucose consumption % (culture period; hr) | Alcoholic fermentability % (culture period; hr) |
| None (control) | 30 (6) 40 (50) | 25 (6) 25 (50) |
| Castor oil | 100 (6) | 100 (6) |
| Soybean oil | 100 (7) | 100 (7) |
| Olive oil | 100 (7) | 100 (7) |
| Tung oil | 100 (7) | 100 (7) |

Table 2 indicates that immobilized cells can maintain normal vital activity (i.e. glucose consumption and alcoholic fermentation) without any inhibition even in the presence of 0.1% of 2-octanol when a solid immobilizing carrier contains a vegetable oil, which is an absorbent for the harmful organic solvent (i.e. 2-octanol), simultaneously with said cells.

EXAMPLE 2

10 ml of Porapak Q (100 to 200 mesh), which was a packing for gas chromatography as well as an absorbent for alcohols, was added to 10 ml of a yeast strain (Saccharomyces uvarum ATCC 26602) which had been cultured in 84 ml of a 2% sterilized aqueous solution of sodium alginate for 16 hours and throughly admixed therewith. The obtained mixture was added dropwise through a nozzled to a 100 mM solution of calcium chloride to thereby form spherical immobilized cells (diameter mm). 20 g of the immobilized cells thus obtained and 0.4 g of calcium chloride were added to 200 ml of a glucose medium in an Erlenmeyer flask of 500 ml in volume and cultured therein at 100 rpm and 30° C. for 16 hours. Then the immobilized cells alone were taken out from the medium and added to a 200 ml of a fresh glucose medium in an Erlenmeyer flask of 500 ml in volume. 0.1% of 2-octanol which was a harmful organic solvent was further added thereto and culture was carried out under the same condition as described above. Table 3 shows the result wherein each value represents a relative % calculated by defining the glucose consumption or alcoholic fermentability in the absence of 2-octanol as 100%. Immobilized cells containing no Porapak Q were employed as a control. Figures in parentheses represent culture periods. After culturing for six hours, the control immobilized cells to which no 2-octanol was added entirely consumed the glucose, thus completing the alcoholic fermentation.

TABLE 3

Effect of 2-octanol on glucose consumption of immobilized cells containing Porapak Q

| Absorbent | Glucose consumption % (culture period: hr) | Alcoholic fermentability % (culture period: hr) |
|---|---|---|
| None (control) | 30 (6) 40 (50) | 20 (6) 25 (50) |
| Porapak Q | 100 (6) | 100 (6) |

Table 3 indicates that the immobilized cells can maintain normal vital activity (i.e. glucose consumption and alcoholic fermentation) without any inhibition even in the presence of 0.1% of 2-octanol when a solid immobilizing carrier contains Porapak Q, which is an absorbent for higher alcohols, simultaneously with the cells.

EXAMPLE 3

Immobilized cells containing vegetable oils and Porapak Q as prepared in Examples 1 and 2, respectively, were repeatedly subjected to batch culture in unsterilized glucose media in flasks to which 0.1% of 2-octanol was added. That is, after completing the first batch culture, each immobilized cells alone were taken out from the medium and added to a fresh unsterilized glucose medium containing 0.1% of 2-octanol and subjected to the second batch culture. This procedure was further repeated, thus carrying out the batch culture six times in total. Table 4 shows the result wherein each value represents a relative % claculating by defining the glucose consumption or alcoholic fermentability of the immobilized cells containing no absorbent for organic solvents in the absence of 2-octanol as 100%. Figures in parentheses indicate culture periods. After culturing for six hours, the immobilized cells containing no absorbent in the absence of 2-octanol entirely consumed the glucose, thus completing the alcoholic fermentation.

TABLE 4

Glucose consumption and alcoholic fermentability of immobilized cells containing absorbent for organic solvents in repeated batch culture in unsterilized medium

| Immobilized cells containing absorbent | Glucose consumption % (culture period: hr) | Alcoholic fermentability % (culture period: hr) | Infectious microbes | Glucose consumption % (culture period: hr) | Alcoholic fermentability % (culture period: hr) | Infectious microbes |
|---|---|---|---|---|---|---|
| | First batch culture | | | Second batch culture | | |
| Immobilized cells containing castor oil | 100 (6) | 100 (6) | none | 100 (5) | 100 (5) | none |
| Immobilized cells containing Porapak Q | 100 (6) | 100 (6) | none | 100 (5) | 100 (5) | none |
| | Third batch culture | | | Fourth batch culture | | |
| Immobilized cells containing castor oil | 100 (5) | 100 (5) | none | 100 (5) | 100 (5) | none |
| Immobilized cells containing Porapak Q | 100 (5) | 100 (5) | none | 100 (5) | 100 (5) | none |

| Immobilized cells containing absorbent | Glucose consumption % (culture period: hr) | Alcoholic fermentability % (culture period: hr) | Infectious microbes |
|---|---|---|---|
| | Sixth batch culture | | |
| Immobilized cells containing castor oil | 100 (7) | 100 (7) | none |
| Immobilized cells containing Porapak Q | 100 (5) | 100 (5) | none |

Table 4 indicates that both the immobilized cells containing castor oil and those containing Porapak Q exhibit normal glucose consumption and alcoholic fermentability in batch culture repeated six times in an unsterilized medium containing 0.1% of 2-octanol without any growth of infectious microbes.

What is claimed is:

1. A composition comprising:
   spherically immobilized microbial cells which comprise microbial cells, an absorbent for an antimicrobial organic solvent, and a gel carrier, wherein said microbial cells are prepared by combining said absorbent and said gel carrier in an aqueous solution so as to form spherically immobilized microbial cells that maintain the vital activity of said microbial cells; and
   a culture medium that contains said spherically immobilized microbial cells and that contains an antimicrobial organic solvent wherein the antimicrobial organic solvent is 2-octanol, toluene, or benzene.

2. A composition as defined in claim 1, wherein the microbial cells are bacteria, yeasts, or fungi.

3. A composition as defined in claim 1, wherein the absorbent is a lipid, an organic solvent absorptive carrier, a glyceride or a fatty acid.

4. A composition as defined in claim 1, wherein the absorbent is a long-chain hydrocarbon, a wax ester, a phospholipid, a glycolipid, active carbon, acid clay, alumina, silica gel, castor oil, soy bean oil, olive oil, tung oil, linseed oil, sesame oil, peanut oil, rape seed oil, oleic acid, erucic acid, linolic acid, linolenic acid, or ricinoleic acid.

5. A composition as defined in claim 1, wherein the gel carrier is an alginate, K-carrageenan, agar, collagen, gelatin, a polyacrylamide, a photocrosslinked resin, or a urethane polymer.

6. A composition as defined in claim 1, wherein the diameter of the spherically immobilized microbial cells is about 3 mm.

7. A composition as defined in claim 1, wherein the amount of absorbent is from 0.1 to 15% of the amount of gel carrier used.

8. The composition as defined in claim 1, wherein the absorbent is a lipid, synthetic exchange resin or a fatty acid.

9. A composition comprising:
spherically immobilized microbial cells which comprise microbial cells, an absorbent for an antimicrobial organic solvent, and a gel carrier, wherein said microbial cells are prepared by combining said absorbent and said gel carrier in an aqueous solution so as to form spherically immobilized microbial cells that maintain the vital activity of said microbial cells; and
a culture medium that contains said spherically immobilized microbial cells and that contains an antimicrobial organic solvent wherein the microbial cells are Saccharomyces cerevisiae or Saccharomyces uvarum, wherein the absorbent is a vegetable oil or an organic solvent absorptive carrier, wherein the gel carrier is an alginate, and wherein the antimicrobial organic solvent is 2-octanol.

10. A composition as defined in claim 8, wherein the diameter of the spherically immobilized microbial cells is about 3 mm.

11. A composition as defined in claim 10, wherein the amount of absorbent is from 0.1 to 15% of the amount of gel carrier used.

12. A method for culturing microbial cells which comprises:
culturing spherically immobilized microbial cells which comprise microbial cells, an absorbent for an antimicrobial organic solvent, and a gel carrier, wherein said microbial cells are prepared by combining said absorbent and said gel carrier in an aqueous solution so as to form spherically immobilized microbial cells that maintain the normal vital activity of said microbial cells, in a culture medium containing an antimicrobial organic solvent wherein the microbial cells are Saccharomyces cerevisiae or Saccharomyces uvarum, wherein the absorbent is a vegetable oil or an organic solvent absorptive carrier, wherein the gel carrier is an alginate, and wherein the antimicrobial organic solvent is 2-octanol.

13. A method for culturing microbial cells as defined in claim 12, wherein the spherically immobilized microbial cells are cultured in a medium containing glucose, and wherein the microbial cells consume said glucose.

14. A method for culturing microbial cells as defined in claim 12, wherein the microbial cells produce alcohol through fermentation.

15. A method for culturing microbial cells which comprises:
culturing spherically immobilized microbial cells which comprise microbial cells, an absorbent for an antimicrobial organic solvent, and a gel carrier, wherein said microbial cells are prepared by combining said absorbent and said gel carrier in an aqueous solution so as to form spherically immobilized microbial cells that maintain the normal vital activity of said microbial cells, in a culture medium containing an antimicrobial organic solvent wherein the antimicrobial organic solvent is 2-octanol, toluene, or benzene.

16. A method for culturing microbial cells as defined in claim 15, wherein the microbial cells are bacteria, yeasts, or fungi.

17. A composition as defined in claim 15, wherein the absorbent is, a phospholipid, a glycolipid, a long-chain hydrocarbon, a wax ester, active carbon, acid clay, alumina, silica gel, a castor oil, soy bean oil, olive oil, tung oil, linseed oil, sesame oil, peanut oil, rape seed oil, oleic acid, erucic acid, linolic acid, linolenic acid, or ricinoleic acid.

18. A method for culturing microbial cells as defined in claim 15, wherein the gel carrier is an alginate, K-carrageenan, agar, collagen, gelatin, a polyacrylamide, a photocrosslinked resin, or a urethane polymer.

19. A method for culturing microbial cells as defined in claim 16, wherein the spherically immobilized microbial cells are cultured in a medium containing glucose, and wherein the microbial cells consume said glucose.

20. A method for culturing microbial cells as defined in claim 16, wherein the microbial cells produce alcohol through fermentation.

21. The composition as defined in claim 15, wherein the absorbent is a lipid, synthetic exchange resin or a fatty acid.

* * * * *